(12) United States Patent
Palmery et al.

(10) Patent No.: US 6,645,899 B1
(45) Date of Patent: Nov. 11, 2003

(54) METHOD OF THE REMOVAL OF THE TEMPLATING AGENT FROM SYNTHETIC ZEOLITES

(75) Inventors: Stefano Palmery, Milan (IT); Fausto Genoni, Milan (IT); Guido Spano', Novara (IT); Leonardo Dalloro, Bollate (IT); Alberto Cesana, Carate Brianza (IT); Roberto Buzzoni, San Mauro Torinese (IT)

(73) Assignee: Enichem S.p.A., San Donato Milanese (IT)

( * ) Notice: Subject to any disclaimer, the term of this patent is extended or adjusted under 35 U.S.C. 154(b) by 96 days.

(21) Appl. No.: 09/712,213

(22) Filed: Nov. 15, 2000

(30) Foreign Application Priority Data

Nov. 19, 1999 (IT) .......................................... MI99A2424

(51) Int. Cl.[7] ................................................ B01J 29/06
(52) U.S. Cl. ............................ 502/85; 502/64; 502/71; 502/77; 423/702; 423/705; 423/713
(58) Field of Search ............................ 502/85, 64, 71, 502/77; 423/702, 705, 713

(56) References Cited

U.S. PATENT DOCUMENTS

| | | | |
|---|---|---|---|
| 4,916,097 A | * | 4/1990 | Chu et al. ..................... 502/62 |
| 5,066,630 A | * | 11/1991 | Kitamura et al. ........... 423/700 |
| 5,143,879 A | | 9/1992 | Whitehurst |
| 5,425,934 A | | 6/1995 | Malla et al. |
| 5,681,789 A | * | 10/1997 | Saxton et al. ................. 502/77 |

FOREIGN PATENT DOCUMENTS

EP  0 735 017 A1  10/1996

OTHER PUBLICATIONS

Patent Abstracts of Japan, vol. 1998, No. 03, Feb. 27, 1998, JP 09 295812, Nov. 18, 1997.
Patent Abstracts of Japan, vol. 1998, No. 06, Apr. 30, 1998, JP 10 043599, Feb. 17, 1998.
Derwent Publications, AN–1999–509191, CN 1 220 301, Jun. 23, 1999.
G.P. Heitmann, et al., Journal of Catalyts, "Catalytically Active Sites for the Beckmann Rearrangement of Cyclohexanone Oxime to $\epsilon$–Caprolactam," (1999), 386, pp. 12–19.

* cited by examiner

*Primary Examiner*—Tom Dunn
*Assistant Examiner*—Christina Ildebrando
(74) *Attorney, Agent, or Firm*—Oblon, Spivak, McClelland, Maier & Neustadt, P.C.

(57) ABSTRACT

The present invention relates to a method for the removal of the templating agent from synthetic zeolites in general and in particular from silicalite, titanium silicalite and from composite materials containing zeolites and for their activation as catalysts.

Figure 1:
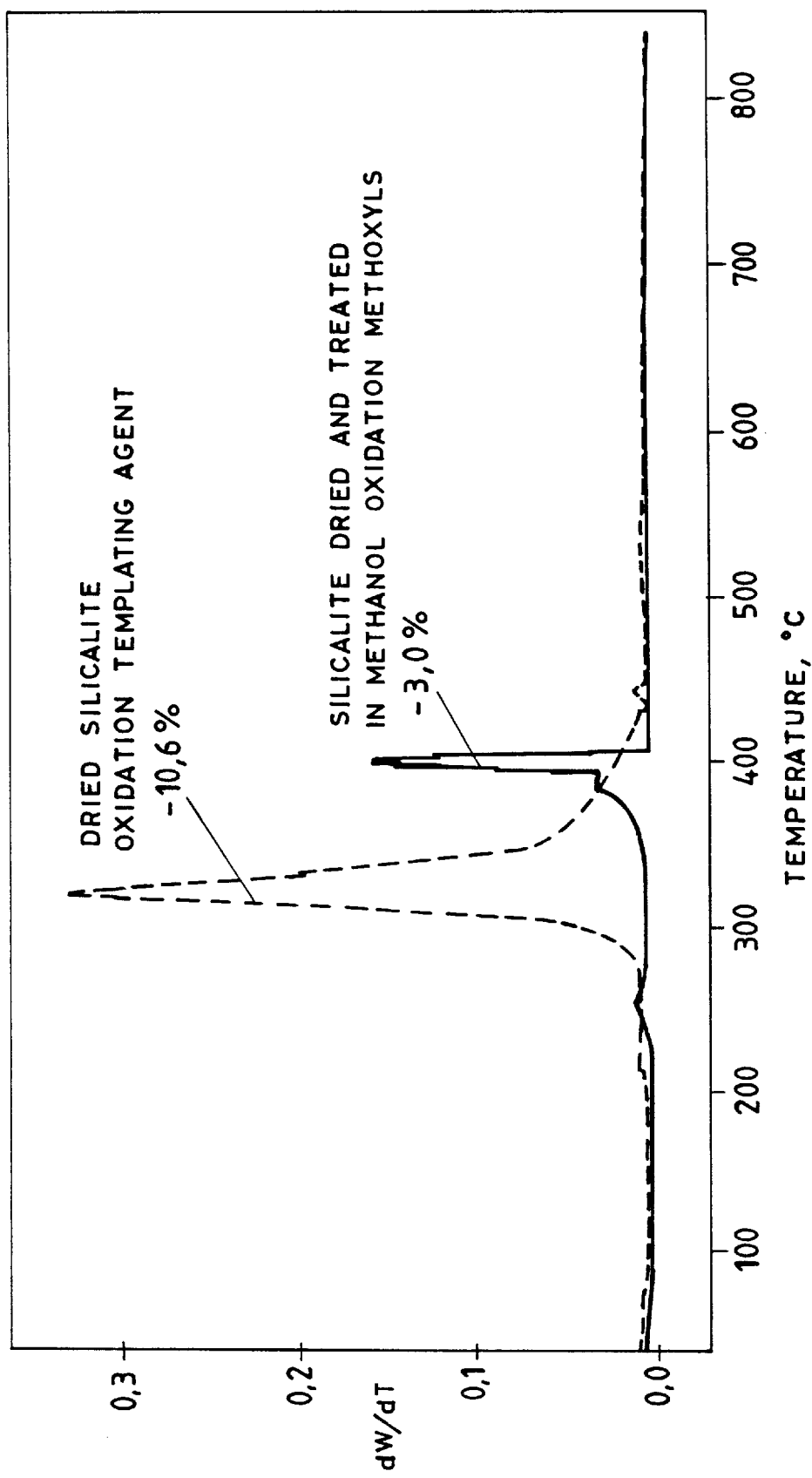

The method consists in treating the above materials with solvents in vapor phase and at a low temperature.

32 Claims, 1 Drawing Sheet

METHOD OF THE REMOVAL OF THE TEMPLATING AGENT FROM SYNTHETIC ZEOLITES

The present invention relates to a method for the removal of the templating agent from synthetic zeolites in general, and in particular from silicalite-1 (S-1) and titanium silicalite-1 (TS-1), and from composite materials containing zeolite.

More specifically, the present invention relates to a method for the removal of the templating agent from synthetic zeolites and for their activation as catalysts, which consists in treating the above materials with solvents, in vapor phase and at a low temperature.

The invention also relates to the materials obtained by means of the above processes and to the catalytic processes in which they are used as catalysts.

Zeolites and zeolitic materials are known in literature as basic components for the preparation of catalysts which can be used in numerous reactions of industrial interest.

For example, zeolites of the MFI type with a low content of trivalent hetero-elements, are known in literature as basic material for the preparation of catalysts which can be used in the transposition reaction of oximes to amides (EP 242,960).

Titanium-Silicalites TS-1 are known as materials for the preparation of catalysts which are used in many oxidation reactions among which ammoximation reactions (U.S. Pat. Nos. 4,410,501; 4,794,198).

Beta zeolites are known as materials for the preparation of catalysts which are used in alkylation reactions (EP 687,500).

ZSM-12 zeolites are used in various acid catalysis reactions among which transalkylation reactions of aromatics (U.S. Pat. No. 5,347,061).

Synthetic zeolites are generally prepared by reacting a silicon compound, such as tetra-alkyl-orthosilicate or an inorganic silica source, optionally mixed with another suitable alkoxide of an element different from silicon or a corresponding inorganic compound, in the presence of an organic templating agent, such as a tetra-alkylammonium hydroxide; the reaction mixture may also contain an inorganic base, such as sodium hydroxide.

The reaction mixture is subjected to hydrothermal synthesis in an autoclave at high temperatures until zeolite crystals are formed.

The crystals are then separated from the mother liquor, washed with water and dried.

The zeolite thus obtained contains the organic templating agent which is trapped inside the pores of the zeolite itself.

The zeolites prepared in the presence of an organic templating agent are initially inactive as catalysts.

It is believed that the lack of catalytic activity is due to the presence of the molecules of organic templating agent adsorbed on the internal and external surface of the zeolite.

The removal of the templating agent and consequent activation of the zeolite for use as catalyst generally take place at high temperatures, by calcining the crystals in air, at 550° C., for times ranging from 0.25 to 72 h (U.S. Pat. No. 4,410,501).

It is known however that this method can cause degradation of the crystalline structure or induce more or less marked surface modifications in relation to the different stability of the various types of zeolites.

This leads to the importance of developing alternative methods for removing the templating agent, using lower temperatures.

With these objectives, the U.S. Pat. No. 5,425,934, for example, describes a method for the dealumination and selective removal of organic templating agents from synthetic zeolites. The method consists in the treatment of a zeolite characterized by a ratio $SiO_2/Al_2O_3$ of at least 7:1, with an alcohol (methanol) and an acid (hydrochloric acid), in liquid phase and at a low temperature.

Operating according to the method of U.S. Pat. No. 5,425,934, however, a partial, even if selective, removal of the templating agent is obtained, from a particular group of pores of the zeolitic structure and, moreover, no information is provided as to the catalytic activity of the zeolites obtained by means of this process.

U.S. Pat. No. 5,681,789 discloses a method for the activation of zeolites, containing titanium, which are used as catalysts. In particular, the method consists in treating the zeolites with ozone, at low temperatures and for a time sufficient to reduce the quantity of organic templating agent contained therein.

The zeolites obtained by means of this process, although having catalytic capacities comparable to those obtained by calcination, still contain a substantial quantity of organic templating agent.

A method has now been found which allows the templating agent to be effectively removed from synthetic zeolites and at the same time obtaining materials with catalytic properties similar or improved with respect to those typical of a zeolite prepared according to the methods described in the known art.

In particular, an object of the present invention relates to a process for the removal of the templating agent from synthetic zeolites and for their activation as catalysts, characterized in that the zeolites are preheated to the treatment temperature in a stream of nitrogen and treated in vapor phase with methanol, methyl esters or methyl halides, optionally diluted with another inert solvent, for example toluene, at molar concentrations ranging from 20 to 100%, at temperatures ranging from 250° to 380° C., preferably at atmospheric pressure, obtaining a contact time ranging from 0.1 to 5 s and prolonging the treatment for a time ranging from 0.25 to 72 hours. The contact time refers to the time necessary for the reaction mixture in vapor phase to pass through the catalyst in the reactor.

Reagents for the treatment which can be used are methanol, methyl esters or methyl halides. Among methyl esters, those of acids with up to 4 carbon atoms are particularly suitable; preferred are dimethyl carbonate, methyl acetate and methyl formiate. Among the methyl halides, methyl iodide is preferred.

At the end of the treatment the catalyst is flushed with nitrogen.

The treatment can be carried out in a fixed bed or fluid bed reactor.

All synthetic zeolites can be treated with the process of the invention, in particular the group of porous zeolites of the MFI, MTW and BEA type, in which a portion of silicon atoms of the crystalline structure can be substituted by aluminum atoms or another trivalent element, titanium or another tetravalent element, or vanadium and which contain an organic templating agent in the pores of their structure.

In particular the zeolites which can be conveniently treated with the method of the invention comprise the group of microporous crystalline silicates which contain only silicon and oxygen or also, optionally, at least either titanium or aluminum, in their lattice.

The zeolites from which the templating agent can be removed by means of the method of the present invention can generally be obtained by hydrothermal synthesis in which compounds based on silicon and, optionally, Titanium or Aluminum (all for example in the form of alkoxides or oxides) are reacted at reasonably high temperatures for periods ranging from a few hours to several days in the presence of a base or quaternary ammonium salt, which acts as organic templating agent, and optionally an inorganic base.

Particularly preferred are synthesis zeolites commonly defined as: Silicalite (S-1), having a structure of the MFI type and described in patent EP 242,960, Titanium-Silicalite (TS-1), having a structure of the MFI type and described in U.S. Pat. Nos. 4,410,501 and 4,794,198, Beta Zeolite, having a structure of the BEA type and described in patent EP 687,500, ZSM-5 Zeolite, having a structure of the MFI type and described in U.S. Pat. Nos. 3,702,886 and 5,705,726, ZSM-12 Zeolite, having a structure of the MTW type and described in U.S. Pat. No. 3,832,449.

In addition they contain the organic templating agent used for their synthesis.

The templating agent can be any organic compound capable of directing the construction of the zeolitic structure; as is known in the art, the pore dimension, the structure of the channels and, basically, the arrangement of the atoms in the lattice of the zeolites are influenced by the type, dimension and structure of the templating agent.

A typical example of organic templating agents are salts and bases of quaternary ammonium such as tetrapropylammonium hydroxide or tetraethylammonium hydroxide, although other compounds such as for example corona ethers, tri-, di- and mono-alkylamines, diamines, cyclic and polycyclic amines, amines and polyamines, can also be conveniently used in the preparation of zeolites which can be treated according to the process of the invention.

When subjected to the process of the invention, the synthesis zeolites can be in powder form, as is the case after preparation in crystalline phase, or they can have already been subjected to mixing and forming processes with suitable inorganic binding materials, such as for example silica or alumina or their precursors also of an organic nature, as described in the art. These processes make the zeolites suitable for industrial use in catalytic processes and consist in giving them a suitable physical form to be used in the reactor (pellet, microsphere, etc.). The weight proportion between zeolite and ligand or carrier can vary from 1:9 to 9:1, but preferably from 3:7 to 7:3.

Alternatively, the zeolite can be mixed with ligands and suitably treated after removal of the templating agent.

The synthesis zeolites are put in contact with the treatment mixture, consisting for example of methanol and toluene, for a time and at a temperature which allow the whole or majority of the organic templating agent to be removed.

However, it is not essential to completely remove the organic templating agent to obtain a catalytic activity which is better or comparable to that of a synthesis zeolite which has been calcined with the conventional methods to eliminate the templating agent.

The degree of removal of the organic templating agent is conveniently controlled by subjecting samples of zeolite treated according to the process of the invention, to thermogravimetric analysis (TG).

The TG technique is an evaluation method which measures the variation in weight of a sample, immersed in a controlled atmosphere, and subjected to a temperature increase, typically with a constant gradient and within a range varying from room temperature to 850° C.

The variation in weight of the zeolite as obtained from the synthesis can be attributed to the decomposition and combustion of the residual templating agent which, in the case of Silicalite-1, takes place at a temperature ranging from 250 to 450° C., but which can vary depending on the type of structure and templating agent.

The samples subjected to drying treatment alone, which still contain therefore all the templating agent, show, upon TG analysis, the maximum weight variation, whereas the samples subjected to calcination show an insignificant loss in weight, due to the fact that the templating agent has already been eliminated by the calcination treatment.

The samples treated according to the process of the invention show a higher loss in weight than the calcined product, but the templating agent however should be considered as having been entirely eliminated. TG analysis in fact allows this loss in weight to be definitely attributed to the methoxyls generated in the zeolite by the reagents used for the treatment.

Operating according to the process of the invention, it is possible to totally remove the templating agent from S-1, almost totally from TS-1 and for the most part from acid zeolites such as Beta, ZSM-12 and ZSM-5.

The removal of the templating agent can also be controlled by means of the porosimetric technique which allows the internal volume of the zeolitic channels (micropore volume) to be evaluated by means of absorption measurements of a gas (argon), under certain conditions.

The micropore volume of the samples treated according to the process of the invention are only slightly reduced with respect to the typical volume of the various zeolitic structures, thus confirming at the same time the removal of the templating agent and the presence of methoxyls. The non-treated samples, in which the templating agent is still present, have, on the other hand, a micropore volume which is practically zero (zeolitic channels blocked by the templating agent).

After the treatment of the invention, the zeolites surprisingly have a better catalytic activity with respect to the same materials treated according to the conventional calcination method.

In particular, in the case of S-1, improved catalytic performances are obtained in the transposition reaction of cyclohexanone oxime to $\epsilon$-caprolactam.

These performances are maintained even after subsequent repeated thermo-oxidative treatment, which is necessary to compensate the deterioration in the catalytic performances during the reaction.

The deterioration process, in fact, makes it necessary for the catalytic activity to be periodically reintegrated by means of the combustion of the pitches formed during the reaction, which obstruct the pores of the catalyst impeding access of the reagent to the active centers.

The regeneration takes place by oxidizing treatment in a stream of air (optionally diluted with nitrogen), at a temperature ranging from 450 to 550° C., preferably from 450 to 500° C.

The process of the invention, in the specific case of S-1 for the Beckmann catalytic transposition of cyclohexanone oxime to $\epsilon$-caprolactam, can be carried out in the same reactor destined for the reaction. This reaction, in fact, takes place in vapor phase at temperatures ranging from 300 to 400° C., using methanol as solvent, optionally diluted with other compounds (for example toluene).

In fact, it has been surprisingly observed that if the catalyst containing the templating agent is charged into the reactor, as it is when it arrives from the synthesis, and operating under reaction conditions, the templating agent is effectively removed from the catalyst during the reaction and a catalyst having improved performances is produced.

The process of the invention can be advantageously applied to TS-1 for the ammoximation of cyclohexanone to cyclohexanone oxime; in fact it has been observed that by charging the reactor with a catalyst treated according to the present invention and subsequently calcined, better performances are obtained with respect to those of a catalyst simply subjected to conventional calcination treatment.

The process of the invention comprises preheating the catalyst to the treatment temperature in a stream of nitrogen and treating it with suitably vaporized treatment reagents.

At the end of the treatment the catalyst is flushed with nitrogen.

The treatment is generally carried out at temperatures ranging from 250° to 380° C., at atmospheric pressure, effecting a contact time of the treatment reagents ranging from 0.1 to 5 s; the treatment is prolonged for a time ranging from 0.25 to 72 hours.

The reagent for the treatment consists of methanol, methyl esters or methyl halides, optionally diluted with another inert solvent, for example toluene, at concentrations ranging from 20 to 100% molar. The treatment is preferably carried out at atmospheric pressure, at temperatures ranging from 280 to 350° C., with mixtures of methanol/toluene, methyl esters/toluene or methyl halides/toluene, at molar concentrations ranging from 20 to 35%, effecting a contact time ranging from 0.2 to 1 s, prolonging the treatment for a time ranging from 2 to 20 hours.

The catalyst can be treated indifferently in a fixed bed or fluid bed reactor.

After the treatment, according to the process of the invention, the zeolitic materials can be further treated to modify their catalytic properties, for example with thermal treatment or ion exchange.

They can also be subjected, for example, to forming processes to obtain suitable physical forms.

The forming processes can also be effected however before the treatment object of the invention, thus using a zeolite which still contains the templating agent, and the treatment itself can be carried out subsequently.

The fact that the treatment is carried out in the presence of the materials used for the forming, does not affect the advantages obtained by the treatment.

The zeolitic materials obtained according to the process of the invention, can be used as catalysts, also providing better performances, for the same catalytic processes in which they were originally used after being subjected to activation with the conventional methods (calcination).

For example, S-1 can be conveniently used to catalyze the Beckmann transposition of cyclohexanone oxime to caprolactam.

This process takes place in vapor phase at temperatures ranging from 300 to 400° C., using suitable diluents, preferably methanol, as described in detail in patents EP 056, 698, EP 380,364 and MI98/A 002416.

Titanium-Silicalite TS-1 can be conveniently used to catalyze the ammoximation of cyclohexanone to cyclohexanone oxime with hydrogen peroxide and ammonia.

This process takes place in liquid phase at temperatures ranging from 60 to 120° C., using a solvent, in particular ter-butanol, as described in detail in U.S. Pat. No. 4,794,198 and EP 496,385.

Description of the Technical Methods Used to Effect the Treatment and Evaluate Its Effectiveness with Respect to the Characteristics of the Material Obtained and Its Catalytic Performances General Treatment Procedure of the Zeolitic Materials According to the Invention The process of the invention comprises heating the catalyst to the treatment temperature in a stream of nitrogen and treating it with suitably vaporized treatment reagents. At the end of the treatment, the catalyst is flushed with nitrogen.

The treatment is generally effected at temperatures ranging from 250° to 380° C., at atmospheric pressure, effecting a contact time of the treatment reagents ranging from 0.1 to 5 s; the treatment is prolonged for a time ranging from 0.25 to 72 hours.

The reagent for the treatment consists of methanol, methyl esters or methyl halides, optionally diluted with another inert solvent, for example toluene, at concentrations ranging from 20 to 100% molar. The treatment is preferably carried out at atmospheric pressure, at temperatures ranging from 280 to 350° C., with mixtures of methanol/toluene, methyl esters/toluene or methyl halides/toluene, at molar concentrations ranging from 20 to 35%, effecting a contact time ranging from 0.2 to 1 s, prolonging the treatment for a time ranging from 2 to 20 hours.

The catalyst can be treated in a fixed bed or fluid bed reactor, indifferently.

A zeolite can be treated, still containing the templating agent, either pure, as it is when it arrives from synthesis, or mixed and formed with a suitable ligand, indifferently.

General Thermogravimetric Analysis Method

The TG technique is a classical test method which measures the variation in weight of a sample, immersed in a atmosphere controlled by the constant stream of a suitable gaseous mixture (preferably air), and subjected to a temperature increase, typically with a constant gradient and within a range varying from room temperature to 850° C.

The thermo-analytic system METTLER TA3000 was used for the measurements, consisting of a METTLER M3 weighing system and an oven, controlled by a microprocessor.

The analysis is carried out on 15÷30 mg of sample, contained in a platinum crucible, positioned on the plate of the scale immersed in the oven; the sample is flushed with air (30 Nml/min), previously dried and decarbonated with molecular sieves ZANDER MSTE, and heated from room temperature up to 850° C., with a heating rate of 4° C./minute.

The data indicated in the tables of the examples represent the loss in weight undergone by the sample, calculated as percentage with respect to the weight of the dry sample measured at 200° C. (at this temperature the physisorbed solvents were eliminated and the results are repeatable).

The weight variation of the sample coming from the synthesis, well washed and dried, can be attributed to the decomposition and combustion of the residual templating agent, which takes place, in the case of Silcalite-1, at a temperature of about 320° C., as can be seen from the TG graph (FIG. 1), but it may vary in relation to the type of structure and templating agent. The samples subjected to drying treatment alone, which therefore contain all of the templating agent, show the maximum weight variation upon TG analysis, whereas the samples subjected to calcination show an insignificant loss in weight, owing to the fact that the templating agent has already been eliminated by the calcination treatment.

The effectiveness of the treatment of the invention is therefore evaluated, for each type of material, by comparing the results of the analysis of the dried sample (containing the whole templating agent) and the calcined product (templating agent absent) with that of the treated sample.

It has been observed that, although often the loss in weight during the TG analysis of some of the samples treated is not zero, as in the case of the calcined product, the templating agent should in any case be considered as having been completely eliminated. This is due to the fact that, during the treatment of the invention, the methanol also reacts with the hydroxyls present in the zeolite, for example with the silanols (≡Si—OH groups) with the formation of methoxyls (—O—CH$_3$): therefore on the one hand the zeolite loses weight due to the elimination of the templating agent, and on the other hand it gains weight owing to the substitution of an H with a CH$_3$. The loss in weight registered during the TG analysis of a treated sample depends on the combustion of methoxyls, which takes place at different temperatures in relation to their nature, but in any case at a temperature substantially different from that of the templating agent (FIG. 1).

The gravimetric result obviously depends on the concentration of the hydroxyls present in the material.

In the case of S-1 the weight of organic product due to the formation of —O—CH$_3$ groups can be valid up to about 3%. FIG. 1 refers to a TG analysis graph (expressed, to demonstrate the phenomenon better, as TG differential, a derivative of the TG signal), of a dried catalyst for which a consistent weight loss (11%) is observed at the temperature in which the combustion of the templating agent takes place. On the contrary, the catalyst treated according to the process of the invention, (for example with methanol or diluted methyl esters) no longer shows this organic mass to be eliminated, which has already been eliminated by the above treatment, but gives other peaks, which identify losses in weight due to the combustion of —CH$_3$ groups.

General Porosimetric Analysis Method

For the measurement of the micropore volume, the Argon adsorption technique was used, which allows better examination within the isotherm range relating to the adsorption in the micropores; the measurement was carried out on an ASAP 2010 instrument of MICROMERITICS.

The sample is previously degassed at 120° C. under vacuum (<10$^{-5}$ Torr) and then subjected to argon absorption at the temperature of liquid Argon (−186° C.), with partial pressures ranging from 10$^{-6}$ to 10$^{-1}$.

The various zeolitic structures are characterized by typical values of the zeolitic channel volume (micropore volume), which in the case of Silicalite S-1 with an MFI structure is about 0.185 cm$^3$/g.

The micropore volume of the samples treated according to the process of the invention is very similar to that characteristic of the different zeolites, confirming the removal of the templating agent; the small differences registered are due to the presence of methoxyls generated by the reagents used for the treatment.

The samples of non-treated zeolites on the other hand have a micropore volume which is practically zero, as the synthesis templating agent blocks the channels.

Operating Procedure of the Catalytic Test for the Transposition in Vapor Phase of Cyclohexanone Oxime (CEOX) to Caprolactam (CPL) in a Fixed Bed Reactor The catalyst (sieved in a size of 42÷80 mesh) is tested in a tubular, fixed bed micro-reactor having the following characteristics: material=glass, length=200 mm, $\emptyset_{int}$=11.5 mm, thermocouple sheath with $\emptyset_{ext.}$=4 mm.

The catalyst for the test (0.5 g) is diluted with granular quartz up to a volume of 2 cm$^3$; this charge is positioned in the reactor between two quartz layers. For an optimum catalytic performance, the CEOX is fed in a solution of three solvents: toluene, methanol and water.

The CEOX solution is preheated before being introduced into the reactor and vaporized and mixed with nitrogen directly in the reactor, before coming into contact with the catalyst.

In the activation phase of the activity test, the catalyst is heated to the reaction temperature in a stream of nitrogen and dried for 1 hour; the mixture of solvents (toluene, methanol and water) is then fed for at least 30 minutes. The actual test begins with sending the CEOX solution onto the catalyst.

The mixture of effluent vapors from the reactor is condensed and samples are collected for evaluating the catalytic performances.

The samples are analyzed by means of gaschromatography and the catalytic performances are evaluated by calculating the CEOX conversion and selectivity to CPL.

Operating Procedure of the Catalytic Test for the Transposition in Vapor Phase of Cyclohexanone Oxime (CEOX) to Caprolactam (CPL) in a Fluid Bed Reactor The catalyst is tested in a fluid bed reactor with the following characteristics: material=AISI 316 steel, length= 500 mm, $\emptyset_{int}$=30 mm, thermocouple sheath with $\emptyset_{ext.}$=2 mm.

The activation procedure of the activity test is the same used for the tests in the fixed bed reactor, but in this case the CEOX and solvents are preheated, vaporized and mixed with nitrogen before being introduced into the reactor.

The effluents of the reactor are condensed and analyzed as described for the tests in a fixed bed reactor.

Operating Procedure for the Regeneration of the Catalyst for the Transposition in Vapor Phase of Cyclohexanone Oxime (CEOX) to Caprolactam (CPL)

When the catalytic test is carried out to test also the regeneration effect, the feeding of the CEOX solution is interrupted at the end of the reaction phase, the mixture of solvents alone is first fed, followed by nitrogen alone.

The reactor is brought to the regeneration temperature and air is then fed, optionally diluted with nitrogen.

At the end of the regeneration, the reactor is flushed with nitrogen.

Operating Procedure of the Catalyst Test for the Direct Oximation in Liquid Phase of Cyclohexanone with Hydrogen Peroxide and Ammonia (Ammoximation) in a Mixed Reactor 0.498 g of catalyst, 9.90 g of cyclohexanone and then 25 cm$^3$ of aqueous ammonia (at 15% by weight) and 25 cm$^3$ of t-butanol, are charged into a jacketed glass reactor, equipped with a mechanical stirrer, in an inert atmosphere.

The suspension is brought to 78° C. and 11.68 g of an aqueous solution of H$_2$O$_2$ at 30.8% by weight are fed, under stirring, in 50 minutes. At the end of the reaction the suspension is filtered and the solution is analyzed by means of gaschromatography.

EXAMPLES

Examples 1–13

The S-1 was prepared according to the procedure described in example 1 in patent application MI98/A 002416.

The material thus obtained was subdivided into various portions in which one was dried at 120° C. in air, another was calcined at 550° C. in air, the remaining portions were treated as described in the general treatment procedure operating under the conditions specified in table 1.

After drying, calcination or each type of treatment, the samples were subjected to TG analysis according to the procedure described above. The results (delta weight %) are indicated beside each type of treatment (table 1).

TABLE 1

TREATMENT OF SILICALITE-1

Treatment conditions

| Ex. | Temp (° C.) | Reagent/ Diluent | Conc. (% mol) | Duration (h) | TG DELTA WT (%) |
|---|---|---|---|---|---|
| 1 | 120 | in air | — | 15 | 10.7 |
| 2 | 550 | in air | — | 4 | 0.1 |
| 3 | 280 | Methanol/Toluene | 35 | 20 | 2.7 |
| 4 | 250 | Methanol/Helium | 20 | 20 | 6.0 |
| 5 | 350 | Methanol/Helium | 20 | 20 | 2.9 |
| 6 | 280 | Methanol/Helium | 20 | 20 | 3.4 |
| 7 | 280 | Methanol/Toluene | 45 | 20 | 2.8 |
| 8 | 280 | Methanol/Toluene | 89 | 20 | 3.0 |
| 9 | 350 | Methanol/Nitrogen | 89 | 0.25 | 2.5 |
| 10 | 280 | Dimethyl Carbonate/ Toluene | 67 | 20 | 3.5 |
| 11 | 290 | Methyl Formate/ Helium | 63 | 72 | 2.5 |
| 12 | 290 | Methyl Acetate/ Helium | 20 | 72 | 2.1 |
| 13 | 350 | Methyl Iodide/ Helium | 40 | 4 | 0.5 (*) |

(*) It has been observed that, when operating with methyl halides, the templating agent decomposes as occurs when operating with methanol and with methyl esters, but the catalyst is not methoxylated after treatment.

Examples 14–16

The TS-1 was prepared according to the procedure described in U.S. Pat. No. 4,410,501.

The material thus obtained was subdivided into three portions of which one was dried at 120° C. in air, another was calcined at 550° C. in air, whereas the remaining portion was treated according to the invention, as described in the general treatment procedure, operating under the conditions specified in table 2.

The samples, after treatment, were subjected to TG analysis according to the procedure described above. The results (delta weight %) are indicated beside each type of treatment (table 2).

TABLE 2

TREATMENT OF TITANIUM SILICALITE-1

Treatment conditions

| Ex. | Temp (° C.) | Reagent/ Diluent | Conc. (% mol) | Duration (h) | TG DELTA WT (%) |
|---|---|---|---|---|---|
| 14 | 120 | in air | — | 15 | 10.6 |
| 15 | 550 | in air | — | 4 | 0.1 |
| 16 | 290 | Methanol/Helium | 20 | 72 | 2.4 |

Examples 17–19

The Beta Zeolite was prepared according to the procedure described in U.S. Pat. No. 3,308,069.

The material thus obtained was subdivided into three portions of which one was dried at 120° C. in air, another was calcined at 550° C. in air whereas the remaining portion was treated according to the invention, as described in the general treatment procedure, operating under the conditions specified in table 3.

The samples, after treatment, were subjected to thermogravimetric analysis according to the procedure described above. The results (delta weight %) are indicated beside each type of treatment (table 3).

TABLE 3

TREATMENT OF BETA ZEOLITE

Treatment conditions

| Ex. | Temp (° C.) | Reagent/ Diluent | Conc. (% mol) | Duration (h) | TG DELTA WT (%) |
|---|---|---|---|---|---|
| 17 | 120 | in air | — | 15 | 13.0 |
| 18 | 550 | in air | — | 4 | 0.1 |
| 19 | 290 | Methanol/Helium | 20 | 72 | 8.6 |

Examples 20–22

The ZSM-5 zeolite was prepared according to the procedure described in U.S. Pat. No. 3,702,886. The material thus obtained was subdivided into three portions of which one was dried at 120° C. in air, another was calcined at 550° C. in air whereas the remaining portion was treated according to the invention, as described in the general treatment procedure, operating under the conditions specified in table 4.

The samples, after treatment, were subjected to TG analysis according to the procedure described above. The results (delta weight %) are indicated beside each type of treatment (table 4).

TABLE 4

TREATMENT OF ZSM-5 ZEOLITE

Treatment conditions

| Ex. | Temp (° C.) | Reagent/ Diluent | Conc. (% mol) | Duration (h) | TG DELTA WT (%) |
|---|---|---|---|---|---|
| 20 | 120 | in air | — | 15 | 9.3 |
| 21 | 550 | in air | — | 4 | 0.1 |
| 22 | 290 | Methanol/Helium | 20 | 72 | 5.2 |

Examples 23–25

The ZSM-12 zeolite was prepared according to the procedure described in U.S. Pat. No. 3,832,449. The material thus obtained was subdivided into three portions of which one was dried at 120° C. in air, another was calcined at 550° C. in air whereas the remaining portion was treated according to the invention, as described in the general treatment procedure, operating under the conditions specified in table 5.

The samples, after treatment, were subjected to thermogravimetric analysis according to the procedure described above. The results (delta weight %) are indicated beside each type of treatment (table 5).

TABLE 5

TREATMENT OF ZSM-12 ZEOLITE

| Ex. | Temp (° C.) | Reagent/ Diluent | Conc. (% mol) | Duration (h) | TG DELTA WT (%) |
|---|---|---|---|---|---|
| 23 | 120 | in air | — | 15 | 9.5 |
| 24 | 550 | in air | — | 4 | 0.1 |
| 25 | 290 | Methanol/Helium | 20 | 72 | 1.9 |

Examples 26–29

The micropore volume of the samples of S-1 treated according to examples 1–2–3 (ex. 26–28) is measured using the absorption technique described above; the micropore volume of a sample of S-1 treated for 20 h at 28° C. with a mixture of methanol at 35% molar in toluene and subsequently calcined for 4 h at 550° C. (ex. 29), is measured with the same technique. The results are indicated in table 6.

TABLE 6

POROSIMETRIC ANALYSIS OF SILICALITE-1

| Ex. | Temp (° C.) | Reagent/ Diluent | Conc. (% mol) | Duration (h) | Micropore Volume (volume zeolitic channels) (ml/g) |
|---|---|---|---|---|---|
| 26 | 120 | in air | — | 15 | 0.05 |
| 27 | 550 | in air | — | 4 | 0.193 |
| 28 | 280 | Methanol/Helium | 20 | 72 | 0.138 |
| 29 | I) 280 Double treatment | Methanol | 20 | 72 | 0.178 |
|    | II) 550 | Air | — | 4 | |

Examples 30–36

Silicalite-1 catalysts were used for the transposition in vapor phase of cyclohexanone oxime (CEOX) to caprolactam (CPL) according to the procedure described above.

The catalytic performances in a fixed bed reactor of S-1 activated according to the traditional method, example 2 (calcination) and the method of the present invention, examples 3–7 and 10, were evaluated according to the procedure described above (ex. 30, 31–35 and 36 respectively).

The results in terms of conversion of cyclohexanone oxime and selectivity to caprolactam, are indicated in table 7.

TABLE 7

CATALYTIC PERFORMANCES OF SILICALITE-1 IN THE TRANSPOSITION OF CYCLOHEXANONE OXIME (CEOX) TO CAPROLACTAM (CPL) IN A FIXED BED REACTOR

| | Conv. CEOX (%) | | Sel. CPL (%) | |
|---|---|---|---|---|
| Ex. | at 1 h | at 25 h | at 1 h | At 25 h |
| 30 | 99.8 | 71.0 | 94.2 | 95.8 |
| 31 | 99.8 | 93.0 | 95.2 | 97.6 |
| 32 | 99.8 | 93.0 | 94.8 | 96.5 |
| 33 | 99.8 | 93.0 | 95.5 | 97.4 |
| 34 | 99.8 | 92.5 | 95.3 | 97.0 |
| 35 | 99.8 | 95.5 | 96.3 | 97.3 |
| 36 | 99.8 | 93.0 | 94.8 | 96.8 |

Temperature = 350° C., WHSV = 4.5 $h^{-1}$; TAU = 0.13 s

Example 37

Following the procedure described above, the catalytic performances of S-1 activated according to the method of the present invention (example 3), were evaluated in a fixed bed reactor, after various reaction cycles with intermediate regenerations.

In particular the catalytic performances were evaluated 1 hour after the beginning of each cycle and after 1, 3, 13 and 26 reaction cycles.

One cycle comprises 3 reaction hours and 3 regeneration hours of the catalyst in air at 450° C.

The results in terms of conversion of cyclohexanone oxime and selectivity to caprolactam, are shown in table 8.

TABLE 8

CATALYTIC PERFORMANCES OF SILICALITE-1 IN THE TRANSPOSITION OF CYCLOHEXANONE OXIME (CEOX) TO CAPROLACTAM (CPL) IN A FIXED BED REACTOR AND WITH REACTION-REGENERATION CYCLES
[1 h after the beginning of the reaction phase]

| | Cycle 1 | Cycle 3 | Cycle 13 | Cycle 26 |
|---|---|---|---|---|
| Ex. | | Conversion CEOX (%) | | |
| Nr. 37 | 99.8 | 99.8 | 99.8 | 99.8 |
| | | Selectivity CPL (%) | | |
| | 95.2 | 95.9 | 96.4 | 96.4 |

Temperature = 350° C.; WHSV = 4.5 $h^{-1}$; TAU = 0.13 s

Examples 38–40

Catalysts of Silicalite-1 were used for the transposition in vapor phase of CEOX to CPL, also operating in a fluid bed reactor, according to the procedure described above.

The catalytic performances of S-1 activated according to the traditional method, example 2 (calcination) and the method of the present invention, example 3, were evaluated according to the procedure described above (examples 38 and 39 respectively). A sample of S-1 treated for 20 h at 280° C. with a mixture of methanol at 35% molar in toluene and subsequently calcined for 4 h at 550° C. (ex. 40), was also tested with the same procedure.

The results in terms of conversion of cyclohexanone oxime and selectivity to caprolactam, are shown in table 9.

TABLE 9

CATALYTIC PERFORMANCES OF SILICALITE-1 IN
THE TRANSPOSITION OF CYCLOHEXANONE OXIME (CEOX)
TO CAPROLACTAM (CPL) IN A FLUID BED REACTOR

| EX. | Temp. (° C.) | WHSV (h$^{-1}$) | TAU (s) | Conv. CEOX (%) at 1 h | | Sel. CPL (%) at 25 h | |
|---|---|---|---|---|---|---|---|
| 38 | 350 | 2.1 | 0.25 | 95.6 | 82.0 | 93.5 | 94.0 |
| 39 | 350 | 2.1 | 0.25 | 98.0 | 97.5 | 96.2 | 97.5 |
| 40 | 350 | 2.1 | 0.25 | 98.8 | 98.0 | 96.2 | 96.0 |

Examples 41–42

The catalytic performances in a fixed bed reactor of S-1 formed with silica at 50%, as described in example 2 of patent application MI98/A 002416, activated according to the traditional method for calcination (ex. 41) and according to the method of the present invention (forming of S-1 containing the templating agent and treatment of the formed catalyst for 20 h at 280° C. with a mixture of methanol at 35% molar in toluene—ex. 42) were evaluated after 3 reaction cycles.

The results in terms of conversion of cyclohexanone oxime and selectivity to caprolactam, are shown in table

TABLE 10

CATALYTIC PERFORMANCES OF SILICALITE-1 IN THE
TRANSPOSITION OF CYCLOHEXANONE OXIME (CEOX) TO
CAPROLACTAM (CPL) IN A FIXED BED REACTOR
AND WITH REACTION - REGENERATION CYCLES

| EX. | Temp. (° C.) | WHSV (h$^{-1}$) | TAU (s) | Conv. CEOX (%) at 1 h cycle 3 | Sel. CPL (%) at 1 h cycle 3 |
|---|---|---|---|---|---|
| 41 | 350 | 4.5 | 0.13 | 99.8 | 95.2 |
| 42 | 350 | 4.5 | 0.13 | 99.7 | 95.8 |

Catalytic cycle = 3 h in reaction + 3 h in regeneration at 450° C. in air

Examples 43–44

Catalysts of Titanium-Silicalite-1 were used for the ammoximation of cyclohexanone in liquid phase, in a mixed reactor, according to the procedure described above.

The catalytic performances of a TS-1 activated by calcination, according to the traditional method, and a TS-1 treated with methanol, according to the method of the present invention, and subsequently calcined, were evaluated.

The results in terms of conversion of the cyclohexanone, selectivity to cyclohexanone oxime and yield with respect to $H_2O_2$, are indicated in table 11.

TABLE 11

CATALYTIC PERFORMANCES OF TITANIUM SILICALITE-1
IN THE AMMOXIMATION OF CYCLOHEXANONE TO
CYCLOHEXANONE OXIME IN A MIXED REACTOR

| EX. | Treatment of Titanium Silicalite TX-1 | CYCLOHEXANONE | | | $H_2O_2$ |
|---|---|---|---|---|---|
| | | Conv. (%) | Sel. (%) | Yield (%) | Yield (%) |
| 43 | In air at 550° C. for 4 h (ex.17) | 71.8 | 78.5 | 56.3 | 54.8 |
| 44 | Double Treatment: I) Methanol/Toluene (20% mol.) at 290° C. for 72 h II) Air at 550° C. for 4 h | 81.9 | 90.3 | 74.0 | 70.6 |

Initial charge of the reactor:
catalyst (TS-1, 2.76% Ti) = 0.498 g, cyclohexanone = 9.90 g, aqueous ammonia (al 15% wt) = 25 cm$^3$, t-butanol = 25 cm$^3$
Temperature: 78° C.
Feeding (in 50 min): $H_2O_2$ (at 30.8% wt in aqu.sol.) = 11.68 g

What is claimed is:

1. A process for removing a templating agent from zeolites, comprising treating the zeolites with a vapor phase comprising at least one member selected from the group consisting of methanol, a methyl ester, or a methyl halide at molar concentrations ranging from 20 to 100% molar, at a temperature ranging 250° to 380° C., for a duration of contact time ranging form 0.1 to 5 s and prolonging the treatment for a duration of time ranging from 0.25 to 72 hours.

2. The process according to claim 1, further comprising calcinating the zeolites.

3. The process according to claim 1, wherein the treating is carried out at a temperature ranging from 280 to 350° C.

4. The process according to claim 1, wherein the vapor phase further comprises an inert solvent at molar concentrations ranging from 20 to 100%.

5. The process according to claim 4, wherein the contact time ranges from 0.2 to 1 s.

6. The process according to claim 4, wherein the methyl ester is at least one member selected from the group consisting of dimethyl carbonate, methyl acetate and methyl formate and the methyl halide is methyl iodide.

7. The process according to claim 4, wherein the treating is carried out in a fixed bed or fluid bed reactor.

8. The process according to claim 4, wherein the synthetic zeolite comprises a group of crystalline microporous silicates.

9. The process according to claim 8, wherein the group of crystalline microporous silicates comprise silicon and oxygen atoms.

10. The process according to claim 9, wherein the synthetic zeolite is Silicalite S-1.

11. The process according to claim 8, wherein the group of crystalline microporous silicates comprise silicon, oxygen atoms and at least one atom of the group consisting of titanium and aluminum.

12. The process according to claim 11, wherein the zeolite is selected from the group consisting of Silicalite S-1, Titanium-Silicalite TS-1, Beta Zeolite, ZSM-5 Zeolite, and ZSM-12 Zeolite.

13. The process according to claim 4, wherein the templating agent is at least one member from the group consisting of quaternary ammonium salt, quaternary ammonium base, tetrapropylammonium hydroxide, and tetraethylammonium hydroxide.

14. The process according to claim 4, further comprising preparing the zeolite in powder form.

15. The process according to claim 4, wherein the vapor phase further comprises an inert solvent at molar concentrations ranging from 20 to 35%.

16. The process according to claim 4, wherein the prolonging of the treatment is performed for a duration of time ranging from 2 to 20 hours.

17. The process according to claim 4, wherein the treating is performed under atmospheric pressure.

18. The process according to claim 4, further comprising forming the zeolite into pellets or microspheres.

19. The process according to claim 1, wherein the contact time ranges from 0.2 to 1 s.

20. The process according to claim 1, wherein the methyl ester is at least one member selected from the group consisting of dimethyl carbonate, methyl acetate and methyl formate and the methyl halide is methyl iodide.

21. The process according to claim 1, wherein the treating is carried out in a fixed bed or fluid bed reactor.

22. The process according to claim 1, wherein the synthetic zeolite comprises a group of crystalline microporous silicates.

23. The process according to claim 22, wherein the group of crystalline microporous silicates comprise silicon and oxygen atoms.

24. The process according to claim 23, wherein the synthetic zeolite is Silicalite S-1.

25. The process according to claim 22, wherein the group of crystalline microporous silicates comprise silicon, oxygen atoms and at least one atom of the group consisting of titanium and aluminum.

26. The process according to claim 25, wherein the zeolite is selected from the group consisting of Silicalite S-1, Titanium-Silicalite TS-1, Beta Zeolite, ZSM-5 Zeolite, and ZSM-12 Zeolite.

27. The process according to claim 1, wherein the templating agent is at least one member from the group consisting of quaternary ammonium salt, quaternary ammonium base, tetrapropylammonium hydroxide, and tetraethylammonium hydroxide.

28. The process according to claim 1, further comprising preparing the zeolite in powder form.

29. The process according to claim 1, wherein the treating is carried out with methanol, methyl ester or methyl halide diluted in an inert solvent, at molar concentrations ranging from 20 to 35%.

30. The process according to claim 1, wherein the prolonging of the treatment is performed for a duration of time ranging from 2 to 20 hours.

31. The process according to claim 1, wherein the treating is performed under atmospheric pressure.

32. The process according to claim 1, further comprising forming the zeolite into pellets or microspheres.

* * * * *